United States Patent [19]

Hagemann et al.

[11] Patent Number: 4,841,089

[45] Date of Patent: Jun. 20, 1989

[54] PROCESS FOR THE PREPARATION OF 4-MERCAPTOBENZONITRILES, AND 4-MERCAPTOBENZONITRILES

[75] Inventors: Hermann Hagemann, Leverkusen; Klaus Sasse, Bergisch Gladbach, both of Fed. Rep. of Germany

[73] Assignee: Bayer Aktiengesellschaft, Leverkusen, Fed. Rep. of Germany

[21] Appl. No.: 937,935

[22] Filed: Dec. 4, 1986

[30] Foreign Application Priority Data

Dec. 5, 1985 [DE] Fed. Rep. of Germany ....... 3543036

[51] Int. Cl.$^4$ .......................................... C07C 121/52
[52] U.S. Cl. ..................................... 558/412
[58] Field of Search ........................................ 558/412

[56] References Cited

U.S. PATENT DOCUMENTS 4,202,791 5/1980 Sato et al. ........................... 252/299

FOREIGN PATENT DOCUMENTS 0193853 9/1986 European Pat. Off. .
2168377 8/1973 France .
2254562 7/1975 France .

OTHER PUBLICATIONS

Justus Liebigs Annalen Der Chemie, Band 716, 1968, Seiten 47–60, Weinheim. Bergstr.; G. Beck et al.; "Nucleophile Substitution an chlorierten Mono- und Dicyan-benzole", *Seiten 47, 55, Berbindung 3a*.
Chemical Abstracts, Band 77, Nr. 3, 17. Jule 1972, Seite 449, Zusammenfassung Nr. 18874n, Columbus, Ohio, U.S.A.; Y. Takikawa et al.: "Reactions of Organic Compounds with Sodium Hydrosulfide in Liquid Ammonia. IV. Reactions of Aromatic Nitriles with Sodium Hydrosulfide in Liquid Ammonia", & Nippon Kagakua Kaishi 1972, (4), 776-70.
Chemical Abstracts, Band 77, Nr. 15,9. Oktober 1972, Seite 383, Zusammenfassung Nr. 101077a, Columbus, Ohio, U.S.A.; Y. Takikawa et al.: "Reaction of Organic Compounds with Sodium Hydrosulfide in Liquid Ammonia. V. Reactions of Aromatic Halocynides with Sodium Hydrosulfide in Liquid Ammonia", & Technol. Rep. Iwate Univ. 1971, 5, 59–65.
Chemical Abstracts, Band 104, Nr. 17, 28. Apr. 1986, Seite 661, Zusammenfassung Nr. 148557y, Columbus, Ohio, U.S.A.; & JP-A-60 163 857 (Hitachi Ltd) 08-2-6-1985.
Nippon Kagaku Kaisha (4), 766 to 777 (1972).

*Primary Examiner*—Anton H. Sutto
*Attorney, Agent, or Firm*—Sprung Horn Kramer & Woods

[57] ABSTRACT

4-Mercaptobenzonitriles are prepared by reacting the appropriate 4-halogenobenzonitrile with sodium sulfide or sodium hydrogen sulfide in the presence of an inert organic solvent, and subsequently acidifying. The 4-mercaptobenzonitriles thus accessible are new, with the exception of the unsubstituted 4-mercaptobenzonitrile, and can be used as intermediates for the preparation of nematic liquid-crystalline products, herbicides and plant-growth regulators.

4 Claims, No Drawings

PROCESS FOR THE PREPARATION OF 4-MERCAPTOBENZONITRILES, AND 4-MERCAPTOBENZONITRILES

The present invention relates to a process for the preparation of 4-mercaptobenzonitriles from 4-halogenobenzonitriles, and new 4-mercaptobenzonitriles.

Hitherto, only the unsubstituted 4-mercaptobenzonitrile is known. This can be prepared by diazotizing 4-aminobenzonitrile, subsequently reacting with a potassium xanthogenate solution, and saponifying the reaction product (see DE-OS (German Published Specification) No. 2,905,992, yield 46%). Furthermore, it is produced in minor amounts during the reaction of 4-chlorobenzonitrile with sodium hydrogen sulphide in the presence of liquid ammonia (see Nippon Kagaku Kaishi (4), pages 766–770 (1972), yield 23%, major product: 4-chloro-thiobenzamide, further product 4-mercaptothiobenzamide).

4-Mercaptobenzonitrile can be reacted with certain cyclohexane derivatives. The products thereby produced are useful as nematic liquid-crystalline products for the preparation of display elements (see DE-OS (German Published Specification) No. 2,905,992).

There is thus a need for a process with which 4-mercaptobenzonitriles can be prepared in a simple manner and with good yields.

A process for the preparation of 4-mercaptobenzonitriles of the formula (I)

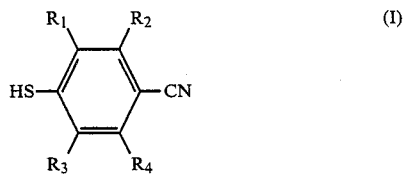

in which
$R_1$, $R_2$, $R_3$ and $R_4$, independently of one another, in each case represent hydrogen, halogen, cyanide, optionally substituted lower alkyl or optionally substituted lower alkoxy, has now been found which is characterized in that 4-halogenobenzonitriles of the formula (II)

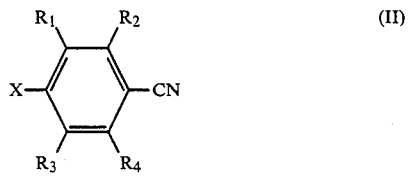

in which
$R_1$–$R_4$ have the meaning stated for formula (I) and
X represents a halogen atom, are reacted with sodium sulfide or sodium hydrogen sulfide in the presence of an inert organic solvent, and are subsequently acidified.

$R_1$, $R_2$, $R_3$ and/or $R_4$ denote halogen in the formulae (I) and (II), this can be, for example, fluorine, chlorine or bromine. Halogen preferably represents chlorine. If $R_1$, $R_2$, $R_3$ and/or $R_4$ denote optionally substituted lower alkyl or lower alkoxy in the formulae (I) and (II), the alkyl portions thereof can be unsubstituted or substituted $C_1$–$C_6$-alkyl radicals. Examples of suitable substituents for the lower alkyl and lower alkoxy are one or more halogen atoms, preferably fluorine atoms. Optionally substituted lower alkyl radicals and lower alkoxy radicals most preferably contain $C_1$–$C_4$-alkyl radicals which are unsubstituted or are substituted by 1 to 3 fluorine atoms. Methyl and trifluoromethyl are most particularly preferred.

Preferably, three of the radicals $R_1$, $R_2$, $R_3$ and $R_4$ in the formulae (I) and (II) represent hydrogen and the fourth of these radicals represents hydrogen, halogen, cyanide, optionally substituted lower alkyl or optionally substituted lower alkoxy.

In formula (II), X preferably represents fluorine, chlorine or bromine, particularly preferably chlorine.

4-Mercaptobenzonitrile, 4-mercapto-5-fluorobenzonitrile, 4-mercapto-5-chlorobenzonitrile, 4-mercapto-5-bromobenzonitrile, 4-mercapto-5-methylbenzonitrile, 4-mercapto-5-trifluoromethylbenzonitrile, 2-chloro-4-mercaptobenzonitrile, 2-trifluoromethyl-4-mercaptobenzonitrile, nitrile and 2-cyano-4-mercaptobenzonitrile, in particular, can be prepared, for example, from the appropriate 4-chlorobenzonitriles by the process according to the invention.

The compounds of the formula (II) to be employed in the process according to the invention are either known or can be prepared in a simple manner which is known per se from the corresponding carboxylic acids.

Sodium sulfide can be employed, for example, in pure form or as it is commercially available, that is to say containing water of crystallization and/or having small amounts of impurities (for example polysulfides and/or thiosulfates). Sodium hydrogen sulfide can likewise be employed in pure form or as an industrial product. When water-containing sodium sulfide or sodium hydrogen sulfide is employed, it is advantageous to remove the water before addition of the compounds of the formula (II), for example by passing an inert gas through the mixture of sodium sulfide or sodium hydrogen sulfide and inert organic solvent at elevated temperatures. 0.8 to 1.5 mol of sodium sulfide can be employed, for example, per mol of the compound of the formula (II). This amount is preferably 1.05 to 1.2 mol. 2 to 4 mol of sodium hydrogen sulfide can be employed, for example, per mol of the compound of the formula (II). This amount is preferably 2.5 to 3 mol. The use of sodium sulfide is preferred.

Examples of suitable inert organic solvents for the process according to the invention are N-methylpyrrolidone, dimethylformamide, hexamethylphosphoric triamide, dimethylacetamide and N-methylcaprolactam, or other N,N-disubstituted open-chain or cyclic carboxamides. Several solvents can also be employed. N-Methylpyrrolidone is preferred. The solvent or solvents are preferably employed in an amount such that the reaction mixture can easily be stirred.

The reaction according to the invention can be carried out at atmospheric pressure, and also at reduced or increased pressure. Atmospheric pressure or slightly increased pressure is preferred, for example a pressure in the range from 1 to 5 bar. Suitable temperatures for the reaction according to the invention are, for example, those from 90° to 180° C. Temperatures from 120° to 160° C. are preferred.

In general, the reaction is complete after 1 to 10 hours. The mixture is then acidifier, for example using aqueous mineral acid, preferably using 5% strength to concentrated hydrochloric acid. The amount of acid can be calculated, so that pH of less than 3, preferably from 0 to 2, is obtained after the addition of the acid.

The acidification can be carried out, for example, at temperatures in the range from −10° to +50° C., temperatures in the range from 0° to 20° C. being preferred here.

The solvent is preferably removed (for example by distillation) from the reaction mixture of the reaction of 4-halogenobenzonitrile with sodium sulfide or sodium hydrogen sulfide, the residue which remains is taken up in water, and any residues which are then present are removed by filtration before starting with the acidification.

After the acidification, particularly when a temperature of below 20° C. is maintained during the acidification, the 4-mercaptobenzoitrile of the formula (I) crystallizes out and can be separated, for example, by centrifuging or filtering. Particularly pure products can be obtained, for example, by taking the 4-mercaptobenzonitrile of the formula (I), isolated in this fashion, up in a solvent, for example in methylene chloride, adding some activated charcoal, filtering this off after a short residence time, drying the filtrate, for example by addition of magnesium sulfate, and subsequently distilling.

The process according to the invention provides the 4-mercaptobenzonitrile of the formula (I) in good yields. These are, in general, above 80% of theory. This is a completely unexpected result, since the nitrile group is preferentially converted to a thioamide group and only a little 4-mercaptobenzonitrile is obtained in the reaction of 4-chlorobenzonitrile with sodium hydrogen sulfide in the presence of liquid ammonia in place of an inert organic solvent (see Nippon Kagaku Kaishi (4), pages 766–770 (1972)).

New 4-mercaptobenzonitriles of the formula (III)

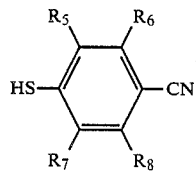

(III)

in which $R_5$, $R_6$, $R_7$ and $R_8$, independently of one another, in each case represent hydrogen, halogen, cyanide, optionally substituted lower alkyl or optionally substituted lower alkoxy, where at least one of these radicals has a meaning other than hydrogen, have also been found.

If $R_5$, $R_6$, $R_7$ and/or $R_8$ in formula (III) denote halogen, then this can, for example, be fluorine, chlorine or bromine. In this case, halogen preferably represents chlorine. If $R_5$, $R_6$, $R_7$ and/or $R_8$ in the formula (III) denote optionally substituted lower alkyl or lower alkoxy, the alkyl portions thereof can be unsubstituted or substituted $C_1$–$C_6$-alkyl radicals. Suitable substituents being, for example, one or more halogen atoms, particularly fluorine atoms. Optionally substituted lower alkyl radicals and lower alkyoxy radicals preferably contain $C_1$–$C_4$-alkyl radicals which are unsubstituted or which are substituted by 1 to 3 fluorine atoms. Methyl and trifluoromethyl are particularly preferred here.

Preferably, three of the radicals $R_5$, $R_6$, $R_7$ and $R_8$ in the formula (III) represent hydrogen and the fourth of these radicals represents halogen, cyanide, optionally substituted lower alkyl or optionally substituted lower alkoxy.

Particularly preferred new 4-mercaptobenzonitriles of the formula (III) are 4-mercapto-5-fluorobenzonitrile, 4-mercapto-5-chlorobenzonitrile, 4-mercapto-5-bromobenzonitrile, 4-mercapto-5-methylbenzonitrile, 4-mercapto-5-trifluoromethylbenzonitrile, 2-chloro-4-mercaptobenzonitrile, 2-methyl-4-mercaptobenzonitrile, 2-trifluoromethyl-4-mercaptobenzonitrile and 2-cyano-4-mercaptobenzonitrile.

The new 4-mercaptobenzonitriles, of the formula (III), according to the invention can be prepared as described above.

The new 4-mercaptobenzonitriles can be used in the same fashion as the unsubstituted 4-mercaptobenzonitrile described initially.

The new 4-mercaptobenzonitriles of the formula (III) can, however, also be reacted with pyri(mi)dine derivatives of the formula (IV)

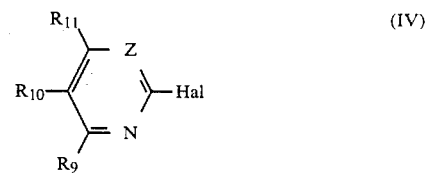

(IV)

in which $R_9$, $R_{10}$ and $R_{11}$, independently of one another, in each case represent halogen, alkyl, optionally substituted alkoxy, halogenoalkyl, alkenyl or optionally substituted amino, $R_9$ and $R_{10}$ or $R_{10}$ and $R_{11}$ together can alternatively represent a fused 3- to 6-membered carbocyclic ring and where at least one of the radicals $R_9$, $R_{10}$ and $R_{11}$ represent alkyl or a part of a 3- to 6-membered carbocyclic ring, Z represents a nitrogen atom or a CH group and Hal represents chlorine or bromine, in the presence of a binder for acids and if appropriate in the presence of a diluent, at 30° to 150° C., and pyri(mi)dyl-thiobenzonitriles of the formula (V)

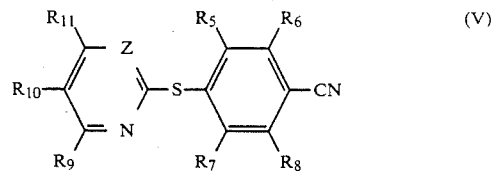

(V)

in which $R_5$, $R_6$, $R_7$, $R_8$, $R_9$, $R_{10}$, $R_{11}$ and Z have the abovementioned meaning can thus be obtained.

The corresponding carboxylic acids can be prepared from the compounds of the formula (V) by saponification of the CN group by conventional methods, and compounds of the formula (VI)

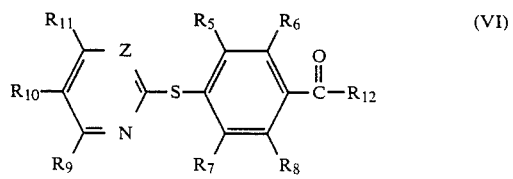

(VI)

in which $R_5$, $R_6$, $R_7$, $R_8$, $R_9$, $R_{10}$, $R_{11}$ *and Z have the abovementioned meaning and* $R_{12}$ *represents halogen, -0-SO$_2$-aryl or the*

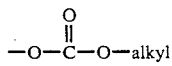

radical, can be prepared from these carboxylic acids or their metal or tertiary ammonium salts in a manner which is known per se, using inorganic acid halides, arylsulphonyl chlorides or alkyl chlorocarbonates, if appropriate in the present of a binder for acids and/or of a diluent, at 0° to 100° C.

Compounds of the formula (VI) can be reacted with the compounds of the formula (VII)

$$H-Y-R_{13} \quad (VII)$$

in which

Y represents oxygen, sulfur or one of the radicals

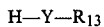

where $R_{14}$ denotes hydrogen or in each case optionally substituted alkyl or alkenyl, and $R_{15}$ denotes hydrogen or in each case optionally substituted alkyl or alkenyl and $R_{13}$ represents optionally substituted saturated or unsaturated alkyl, if appropriate in the presence of a binder for acids and/or of a diluent to given compounds of the formula (VIII)

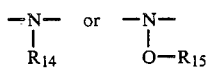

in which $R_5$, $R_6$, $R_7$, $R_8$, $R_9$, $R_{10}$, $R_{11}$, $R_{13}$, Z and Y have the abovementioned meaning.

The compounds of the formula (VIII) have herbicidal, particularly also selective herbicidal, properties and, in addition, also plant growth-regulating properties.

Surprisingly, the compounds of the formula (VIII) display a markedly improved general herbicidal activity towards harmful plants than the pyridyl and pyrimidyl ethers and thioethers, which are known from the state of the art and which are similar compounds chemically and regarding their action. In addition, the compounds of the formula (VIII) display plant growth-regulating activity.

EXAMPLES

Example 1

27.7 g (0.21 mol) of sodium sulfide ×3H$_2$O were mixed with 200 ml of N-methylpyrrolidone and dehydrated at 160° C. using nitrogen. The mixture was then cooled to 140° C. and 27.5 g (0.2 mol) of 4-chlorobenzonitrile were added. After a reaction time of 3 hours at 160° C., the N-methylpyrrolidone was removed by distillation, the residue was taken up in 250 ml of water and filtered, and the filtrate was adjusted to pH 1 using 10% strength aqueous hydrochloric acid, the temperature being kept below 20° C. by cooling. The mixture was then filtered under suction, the filter residue taken up in methylene chloride, activated charcoal was added, the mixture was filtered again, and the filtrate was dried over magnesium sulfate, concentrated and distilled. 23 g (85% of theory) of pure 4-mercaptobenzonitrile of boiling point from 88 to 90° C. at 0.1 mbar and of melting point 48 to 50° C. were obtained in this fashion.

Example 2 to 7

The procedure as described in Example 1 was carried out, but substituted 4-chlorobenzonitriles were employed. The 4-chlorobenzonitriles employed in each case, the reaction products which were isolated and the data which characterized these can be seen from Table 1.

TABLE 1

| Example No. | Starting material (formula (II)) | Reaction product (formula (I)) | Physical data |
|---|---|---|---|
| 2 | X = Cl; $R_1$ = Cl; $R_2$ to $R_4$ = H | $R_1$ = Cl; $R_2$ to $R_4$ = H | M.p.: 64–65° C. |
| 3 | X = Cl; $R_2$ = CH$_3$; $R_1$, $R_3$ and $R_4$ = H | $R_2$ = CH$_3$; $R_1$ $R_3$ and $R_4$ = H | M.p.: 118–120° C. |
| 4 | X = Cl; $R_1$ = CN; $R_2$ to $R_4$ = H | $R_1$ = CN; $R_2$ to $R_4$ = H | M.p.: 127° C. |
| 5 | X = Cl; $R_1$ = CF$_3$; $R_2$ to $R_4$ = H | $R_1$ = CF$_3$; $R_2$ to $R_4$ = H | NMR spectrum: 4.0–4.22 quartet 7.3–7.8 multiplet |
| 6 | X = Cl; $R_2$ = CF$_3$ $R_1$, $R_3$ and $R_4$ = H | $R_2$ = CF$_3$; $R_1$ $R_3$ and $R_4$ = H | M.p.: 72–74° C. |
| 7 | X = Cl; $R_1$ = F; $R_2$ to $R_4$ = H | $R_1$ = F; $R_2$ to $R_4$ = H | NMR Spectrum: 3.9–4.0 doublet 7.3–7.8 multiplet. |

What is claimed is:

1. A 4-mercaptobenzonitrile selected from the group consisting of 4-mercapto-5-fluorobenzonitrile, 4-mercapto-5-chlorobenzonitrile, 4-mercapto-5-bromobenzonitrile, 4-mercapto-5-methylbenzonitrile, 4-mercapto-5-trifluoromethylbenzonitrile, 2-chloro-4-mercaptobenzonitrile, 2-methyl-4-mercaptobenzonitrile, 2-trifluoromethyl-4-mercaptobenzonitrile and 2-cyano-4-mercaptobenzonitrile.

2. A process for the preparation of a 4-mercaptobenzonitrile of the formula

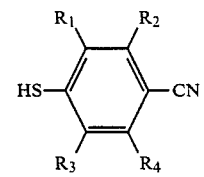

in which $R_1$, $R_2$, $R_3$ and $R_4$, each independently represents hydrogen, unsubstituted or substituted lower alkyl or unsubstituted or substituted lower alkoxy, wherein a 4-halogenobenzonitrile of the formula

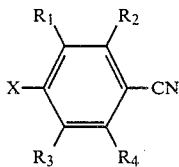

in which $R_1$, $R_2$, $R_3$ and $R_4$ have the abovementioned meanings and

X represents a halogen atom, is reacted at a temperature of 80 to 180° C. with 0.8 to 1.2 moles of sodium sulfide per mole of 4-halogenobenzonitrile or 2 to 4 moles of sodium hydrogen sulfide per mol of 4-halogenobenzonitrile in the presence of an inert organic solvent, and the reaction mixture is subsequently acidified at a temperature of −10° to 50° C. until a pH of less than 3 is reached.

3. A process according to claim 2, wherein $R_1$, $R_2$, $R_3$ and $R_4$ each independently represent hydrogen, unsubstituted $C_1$–$C_6$-alkyl or $C_1$–$C_6$-alkyl which is substituted by halogen atoms, unsubstituted $C_1$–$C_6$-alkoxy or $C_1$–$C_6$alkoxy which is substituted by halogen atoms.

4. A process according to claim 2, wherein the inert organic solvent is selected from N-methylpyrrolidone, dimethylformamide, hexamethylphosphoric triamide, dimethylacetamide and N-methylcaprolactam.

* * * * *